(12) United States Patent
Madsen et al.

(10) Patent No.: US 7,478,636 B2
(45) Date of Patent: Jan. 20, 2009

(54) MULTILUMEN TRACHEAL CATHETER TO PREVENT CROSS CONTAMINATION

(75) Inventors: Edward B. Madsen, Riverton, UT (US); Scott M. Teixeira, Draper, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 503 days.

(21) Appl. No.: 11/198,992

(22) Filed: Aug. 8, 2005

(65) Prior Publication Data

US 2007/0028924 A1 Feb. 8, 2007

(51) Int. Cl.
*A61M 16/00* (2006.01)
(52) U.S. Cl. .............................. 128/207.15; 128/200.26
(58) Field of Classification Search ............ 128/207.14, 128/207.15, 200.26, 911, 912; 604/96.01, 604/101.03
See application file for complete search history.

(56) References Cited

U.S. PATENT DOCUMENTS

| | | | |
|---|---|---|---|
| 2,791,217 A | 5/1957 | Iskander | |
| 4,248,221 A * | 2/1981 | Winnard ................ | 128/207.15 |
| 4,305,392 A | 12/1981 | Chester | |
| 4,327,721 A | 5/1982 | Goldin et al. | |
| 4,469,090 A | 9/1984 | Konomura | |
| 4,584,998 A | 4/1986 | McGrail | |
| 4,607,635 A | 8/1986 | Heyden | |
| 4,637,389 A | 1/1987 | Heyden | |
| 4,840,173 A | 6/1989 | Porter, III | |
| 4,881,542 A | 11/1989 | Schmidt et al. | |
| 5,029,580 A | 7/1991 | Radford et al. | |
| 5,067,497 A | 11/1991 | Greear et al. | |
| 5,140,983 A | 8/1992 | Jinotti | |
| 5,143,062 A | 9/1992 | Peckham | |
| 5,201,310 A | 4/1993 | Turnbull | |
| 5,279,549 A | 1/1994 | Ranford | |
| 5,311,864 A | 5/1994 | Huerta | |
| 5,372,131 A | 12/1994 | Heinen, Jr. | |
| 5,488,949 A | 2/1996 | Kreifels et al. | |
| 5,582,167 A | 12/1996 | Joseph | |
| 5,687,714 A | 11/1997 | Kolobow et al. | |
| 5,803,078 A | 9/1998 | Brauner | |
| 5,819,723 A | 10/1998 | Joseph | |
| 5,832,920 A | 11/1998 | Field | |
| 5,845,634 A | 12/1998 | Parker | |
| D412,984 S | 8/1999 | Cover et al. | |
| 6,062,223 A | 5/2000 | Palazzo et al. | |
| 6,460,540 B1 | 10/2002 | Klepper | |
| 6,550,475 B1 | 4/2003 | Oldfield | |
| 6,612,304 B1 | 9/2003 | Cise et al. | |

(Continued)

FOREIGN PATENT DOCUMENTS

DE 2939794 4/1981

(Continued)

*Primary Examiner*—Steven O Douglas
(74) *Attorney, Agent, or Firm*—James B. Robinson; Scott B. Garrison

(57) ABSTRACT

A multilumen tracheal tube or catheter is disclosed. The tube has a plurality of ingress and egress lumens, each having a suction or discharge port as appropriate. At least one rotatable collar is provided. The collar overlaps each port and is capable of selecting various combinations of suction and discharge ports without increasing the likelihood of cross contaminating any others.

18 Claims, 6 Drawing Sheets

U.S. PATENT DOCUMENTS

| | | |
|---|---|---|
| 6,634,360 B1 | 10/2003 | Flodin |
| 6,668,821 B2 | 12/2003 | Christopher |
| 6,695,810 B2 | 2/2004 | Peacock, III et al. |
| 6,796,309 B2 | 9/2004 | Nash et al. |
| 6,895,966 B2 | 5/2005 | Christopher |
| 7,089,942 B1 | 8/2006 | Grey |
| 2001/0050082 A1 | 12/2001 | Christopher |
| 2002/0014238 A1 | 2/2002 | Kotmel |
| 2002/0077586 A1 | 6/2002 | Madsen et al. |
| 2003/0116162 A1 | 6/2003 | Madsen et al. |
| 2004/0011364 A1 | 1/2004 | Dhuper et al. |
| 2004/0255951 A1 | 12/2004 | Grey |
| 2005/0182291 A1 | 8/2005 | Hirata |
| 2005/0229933 A1 | 10/2005 | McGrail et al. |
| 2006/0207602 A1 | 9/2006 | Kolobow et al. |
| 2007/0028925 A1 | 2/2007 | Madsen et al. |

FOREIGN PATENT DOCUMENTS

| | | |
|---|---|---|
| JP | 2005177134 | 7/2005 |
| WO | WO 93/09833 | 5/1993 |
| WO | WO 99/38548 | 8/1999 |
| WO | WO 2005/009522 | 2/2005 |

\* cited by examiner

MULTILUMEN TRACHEAL CATHETER TO PREVENT CROSS CONTAMINATION

BACKGROUND

The present invention relates to a tracheal tube used for mechanical ventilation of a hospital patient, by insertion of the tube into the trachea of the patient. In particular, the present invention relates to a tracheal tube having means for irrigating and/or evacuating contaminated fluids accumulating above the tracheal tube cuff and thereby reducing the risk of such contaminated fluids entering the lungs of the patient.

Tracheal intubation involves the insertion of a tubular device, known as a tracheal tube, into the trachea of a patient. The tracheal tube passes through the trachea and terminates at a position above the carina, anterior to a position between the second and fourth thoracic vertebrate. Gases may then be introduced through the tracheal tube and into the lungs of the patient.

The primary purposes of tracheal intubation, are to mechanically ventilate the patient's lungs, when a disease prevents the patient from normal, breathing induced ventilation, or to apply anesthetic gases during surgical intervention. In order to create enough air pressure to accomplish such mechanical ventilation and to prevent escape of gases past the tube, it is necessary to seal the passageway around the tracheal tube. A seal may be produced by the use of an inflatable cuff formed integrally with and surrounding the tracheal tube. When the tracheal tube has been introduced into the patient's trachea, the inflatable cuff will normally be located about 3 to 5 centimeters above the carina and within the tube-like trachea.

The inflatable cuff is then inflated so as to engage the wall of the trachea and thereby seal the trachea and prevent gases being introduced through the tracheal tube from simply backing up around the tube. While treatment of this sort has proved successful for patients having chronic or acute respiratory diseases, there is a constant risk of several complications.

In particular, many patients receiving tracheal intubation develop pneumonia, resulting from an infection of the lungs, possibly induced by contaminated, pooled fluids entering the trachea and the lungs after bypassing the epiglottis during intubation. The fluids may be in the form of saliva, blood, secretions, food and stomach contents, even medications. The epiglottis normally operates as a valve which selectively closes the entry into the trachea and lungs, to prevent the introduction of secretions and particulate matter. However, when a tracheal tube is in place, the epiglottis is held in an open position, and secretions which would normally be directed away from the trachea and into the digestive system, instead follow the path of the tracheal tube and pool above the inflatable cuff of the tracheal tube.

The greatest risk of such infectious fluids reaching the lungs is aspiration of these fluids past the tracheal tube cuff during the mechanical ventilation episode. An additional risk in particular is when the need for endotracheal intubation ends, the inflatable cuff of the endotracheal tube is deflated so that the endotracheal tube may be withdrawn, the infectious fluids which have accumulated above the inflatable cuff are released and flow freely into the lower airway where bronchitis and pneumonia may rapidly develop.

To overcome these risks, it is known in the prior art to combine a single lumen suction tube with a tracheal tube. The suction tube is joined to the tracheal tube in a suitable manner, the end of the suction tube terminating at a position above the inflatable cuff. The suction tube provides means for suction or evacuation of any pooled secretions which accumulate in the trachea above the inflatable cuff. However, such prior art devices have the disadvantage that use of a single lumen for the suction tube often causes direct suction to be exerted on the tracheal mucosa which may then result in damage to the mucosa.

U.S. Pat. No. 4,840,173 to Porter III, describes an endotracheal tube having a single lumen suction tube merged thereto. In particular, this patent describes a device wherein the suction tube is laminated to the outside of the ventilation tube, so that the suction tube terminates at a position just above the inflatable cuff. The suction tube includes multiple openings which may be used to evacuate secretions which pool above the inflatable cuff. In addition, the inflatable cuff includes a section immediately adjacent to the end of the suction tube that is less flexible than the rest of the inflatable cuff, to insure that the flexible material of the inflatable cuff is not sucked up against the suction tube openings. The endotracheal tube described in the Porter III patent has the disadvantages noted above, that the single lumen suction tube may exert suction on the tracheal mucosa and thereby cause damage to the mucosa. Further, the Porter III device is of a relatively complex design, requiring difficult processing, resulting in expensive production.

U.S. Pat. No. 5,143,062, issued to Peckham, discloses an endotracheal tube comprising a double lumen through which air may be circulated, creating an indirect gentle suction through a suction eye communicating with the distal ends of the lumens, and located at a position proximal to the inflation cuff. This design, however, does not provide adequate suction necessary for aspirating secretions and is easily occluded.

The above noted patent references fail to adequately address the suctioning of secretions which have pooled above the inflatable cuff in a manner that is sufficient to accomplish the task but is not so strong so as to cause damage to the mucosa. Moreover, these references and other conventional endotracheal and tracheal tubes lack the ability to suction both these secretions, even when a patient is turned according to nationally instituted decubitus prevention protocols. That is, they fail to provide alternative suction capabilities in the event the patient is turned or in the event the desired suction lumen is occluded by secretions.

As the background devices fail to disclose a tracheal tube and suction catheter system having these structural characteristics, the need for such a device is apparent. The instant invention addresses this by providing a multilumen tracheal tube and suction catheter system comprising a device that enables the surgical team to direct suctioning to any number of lumens within the tracheal tube.

SUMMARY OF THE INVENTION

The present invention improves upon a tracheal tube. In one embodiment, a tracheal tube is provided having a cannula that in turn has a distal end and a proximal end. The cannula has at least one ingression lumen within the cannula having a suction port, the suction port is located distal from the proximal end. Also, the cannula has at least one egression lumen within the cannula in non-communication with the at least one ingression lumen, the at least one egression lumen has a discharge port, the discharge port is also located distal from the proximal end. An inlet for introducing an externally applied therapeutic agent or method is provided in the at least one ingression lumen and an outlet for egress of fluids is provided from the at least one egression lumen. In some embodiments, the cannula is made up of a first wall and a second wall which is concentric to the first wall. The first wall surrounds and defines a ventilation lumen which is adjacent a first surface. The first wall is attached at a second surface to a first surface of the second wall by at least two partitions. The at least one ingression lumen is defined by the second surface of the first wall, the first surface of the second wall, and the first surfaces of the at least two partitions. The at least one egression lumen is defined by the second surface of the first wall, the first surface of the second wall, and the second surfaces of the at least two partitions.

In these embodiments, a collar surrounding the cannula and overlapping each inlet and outlet is provided. The collar is positionable so as to selectively enable and disable fluid communication through each lumen between its port and its inlet or outlet. In some embodiments, two collars are provided. A first collar surrounding the cannula and overlapping the inlet, and a second collar surrounding the cannula and overlapping the outlet is provided. Each collar is positionable so as to selectively enable and disable fluid communication through each lumen between its port and its inlet or outlet. An inflatable cuff surrounding the cannula at the distal end is also provided. The inflatable cuff is adapted to seal the trachea of a patient, the inlet and outlet being proximal to the inflatable cuff.

In another embodiment, a tracheal tube is provided. The tracheal tube has a cannula having a distal end and a proximal end. A plurality of ingression lumens are provided within the cannula, each having a suction port located distal from the proximal end and an inlet located proximal to the proximal end. A plurality of egression lumens are also provided within the cannula, each having a discharge port located distal from the proximal end and an outlet located proximal to the proximal end. Each ingression lumen is maintained in fluid non-communication with each egression lumen so as to minimize cross-contamination of any ingression lumen with any egression lumen. A user manipulable selector is provided for selectively enabling and disabling fluid flow through at least one of an ingression lumen, at least one of an egression lumen, or both. The user manipulable selector may be a rotatable collar rotatably affixed to the cannula and overlapping all of the inlets and outlets. The collar itself would contain a first and a second port therethrough. Rotation of the collar aligns the first port with the inlet of a user selected ingression lumen while automatically aligning the second port with the outlet of a corresponding egression lumen. In many embodiments, a guide is coupled to the cannula. the guide overlaps all of the inlets and outlets and has openings aligned with each inlet and outlet. The collar is rotationally attached to the guide. In each embodiment having a guide, a fluid tight seal is provided between the collar and the guide.

In other embodiments, the user manipulable selector is configured as a first and a second rotatable collar. Each is rotatably affixed to the cannula, the first collar overlapping all of the inlets, and the second collar overlapping all of the outlets. Each collar has at least one port therethrough, wherein rotation of the first collar aligns the at least one port with the inlet of a user selected ingression lumen and rotation of the second collar aligns the at least one port with the outlet of a user selected egression lumen. For this embodiment, a guide may be coupled to the cannula overlapping all of the inlets and outlets. The guide would have openings aligned with each inlet and outlet, the first and second collar would be rotationally attached to the guide. In alternative embodiments, a first and a second guide may be coupled to the cannula. The first guide would for example overlap all of the inlets, and the second guide would overlap all of the outlets. Each guide would be provided with openings aligned with each inlet and outlet respectively. The first collar would be rotationally attached to the first guide and the second collar would be rotationally attached to the second guide.

In each embodiment the ingression lumen would enable the introduction of an externally applied therapeutic agent or method to be introduced into a patient within which the tracheal tube is placed. The egression lumen would enable the suctioning of fluids from a patient within which the tracheal tube is placed. Additionally, a ventilation lumen would be provided. In many embodiments, the ingression and egression lumens would be radially disposed about an outer diameter of the ventilation lumen. An inflatable cuff surrounding the cannula at the distal end adapted to seal the trachea of a patient would be provided in many embodiments as well. The inlets and outlets of the cannulas would be proximal to the inflatable cuff. Moreover an inflation lumen for selectively inflating and deflating the inflatable cuff would be provided.

Other objects, advantages and applications of the present invention will be made clear by the following detailed description of a preferred embodiment of the invention and the accompanying drawings wherein reference numerals refer to like or equivalent structures.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims. Those skilled in the art will appreciate that aspects of the various embodiments discussed may be interchanged and modified without departing from the scope and spirit of the invention.

Figure 1:
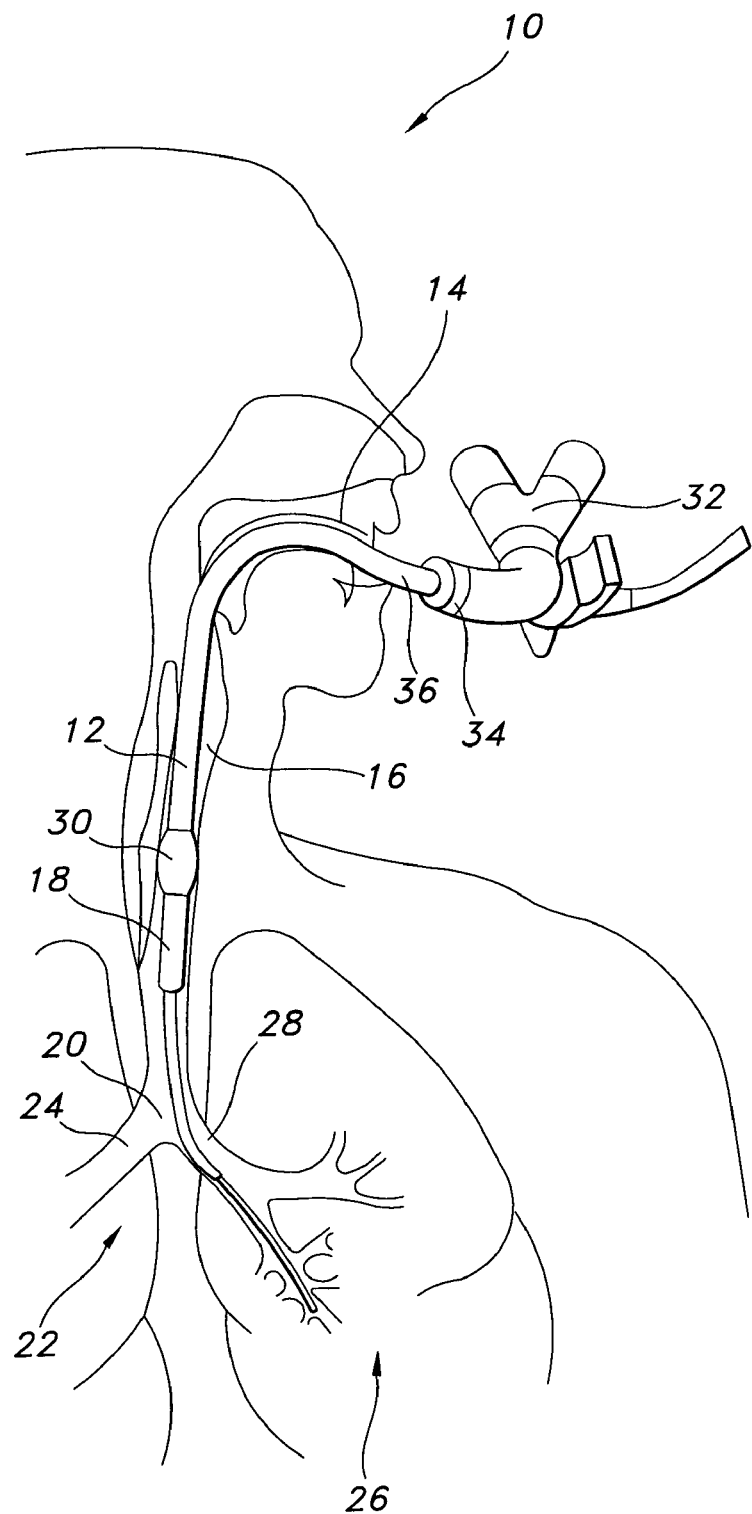
FIG. 1 is diagrammatic illustration of one embodiment of a multilumen catheter placed within a patient in accordance with the present invention.

Referring to FIG. 1, a tracheal tube 12 is depicted extending through the mouth 14 and the trachea 16 of the upper respiratory system of patient 10. The tracheal tube 12 terminates in a distal end 18 well above the point 20 at the first bifurcation of trachea 16 into the right lung 22 through the right mainstem bronchus 24 and into the left lung 26 through the left mainstem bronchus 28. Typical sub-branchings of the mainstem bronchus are shown in FIG. 1 for illustrative purposes in relation to the sub-branching of left mainstem bronchus 24 into left lung 26.

The distal end 18 of tracheal tube 12 is provided with a balloon 30 which, when inflated, engages the walls of trachea 16 to facilitate mechanical ventilation of patient 10 through a connector 32 coupled to a standard tracheal tube adapter 34 at the proximal end 36 of tracheal tube 12. As would be understood by those of skill in the art, air from the ventilating apparatus for patient 10 enters tracheal tube 12 through one leg of the connector 32, and correspondingly, air is returned to the ventilating apparatus from patient 10 through a second leg of the connector.

Figure 2:
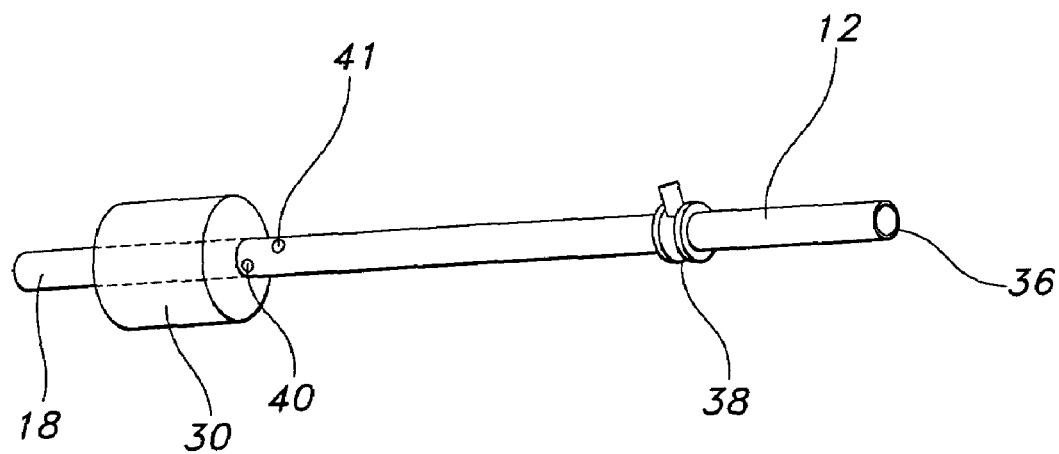
FIG. 2 is an isometric view of the FIG. 1 multilumen catheter in a straightened configuration.

Looking now to FIG. 2, a more detailed view of the tracheal tube 12 may be had. This view depicts the tube 12 in a straightened configuration. A collar 38 is positioned on the tube 12. The collar 38 partially rotates about the tube or cannula and provides the user or medical personnel with an ability to select functionalities as explained in greater detail below.

A plurality of suction ports 40 are provided at desirable locations along the tube 12. In some embodiments, a portion of the suction ports 40 are located above the balloon 30, i.e., between the balloon 30 and the proximal end 36, while another portion are located below the balloon 30, i.e., between the balloon 30 and the distal end 18. Some embodiments may have suction ports 40 on only one side of the balloon 30. Likewise, a plurality of discharge ports 41 are also provided at desirable locations along the tube 12. In some embodiments, a portion of these discharge ports 41 are also located above the balloon 30, while another portion are located below the balloon 30. Similarly, in some embodiments the discharge ports 41 may be located on only one side of the balloon 30.

Figure 3:
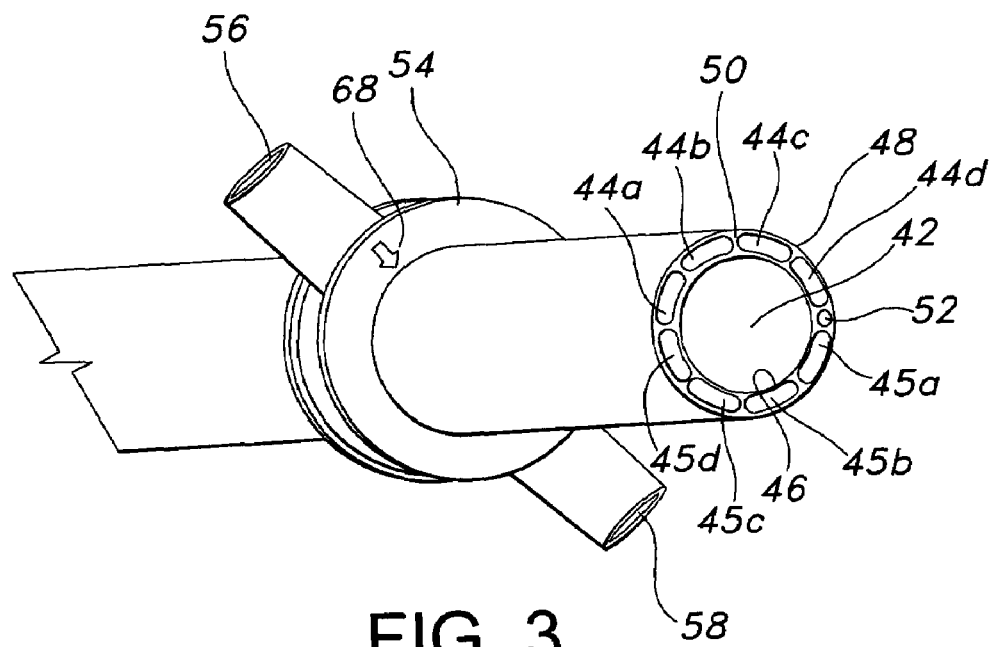
FIG. 3 is a cutaway of the FIG. 1 multilumen catheter viewed through the axial centerline of the multilumen catheter so as to depict the passages therethrough.

As shown in FIG. 3, the tube 12 is configured as a cannula with a plurality of internal lumens that extend at least partially along the length of the tube 12. In the FIG. 3 example, a ventilation lumen 42 is provided at the center of the tube 12. Surrounding the ventilation lumen 42 is a plurality of lumens, including ingression lumens 44 and egression lumens 45. Many embodiments, such as the FIG. 3 embodiment contain a plurality of such lumens 44 and 45 arranged radially about the ventilation lumen 42. A first wall 46 separates the ventilation lumen 42 from each lumen 44 and/or 45. In this embodiment, a second wall 48 forms the exterior wall of the tube 12. A plurality of partitions 50 are provided to separate each lumen 44 and 45 from one another. Each of these walls and partitions may be created via extrusion of the material comprising the tube through an appropriate die during formation of the tube 12 and as such may effectively be considered as a single component having a plurality of lumens situated therein. In any event, the placement of lumens in a tracheal tube is a process that would be understood by those of skill in the art As seen in FIG. 3, additional lumens, for example an inflation lumen 52. The inflation lumen 52 connects the balloon 30 to some means capable of inflating the balloon, thus keeping the tracheal tube 12 adequately sealed and positioned desirably within the trachea 16. It may be seen in this FIG. that the ingression lumens 44 are arranged in a group. Likewise the egression lumens 45 are arranged in a group as well. This is so the collar 38 can align one ingression lumen 44 with one predesignated and corresponding egression lumen 45. As such, the collar 38 is capable of rotating approximately about 180 degrees about the tube 12. A guide 54 may also be provided within which the collar 38 is allowed to rotate.

Looking in more detail at FIG. 3, it can be seen that there are four ingression lumens, designated 44*a-d* and four corresponding egression lumens, designated 45*a-d* respectively. Each of these lumens is diametrically opposed to a corresponding counterpart, that is, lumen 44*a* is diametrically opposite lumen 45*a*, and so on. It should be understood that this labeling is meant only to illustrate that in this embodiment, for every ingression lumen 44 there is a corresponding egression lumen diametrically opposite one another.

Figure 4:
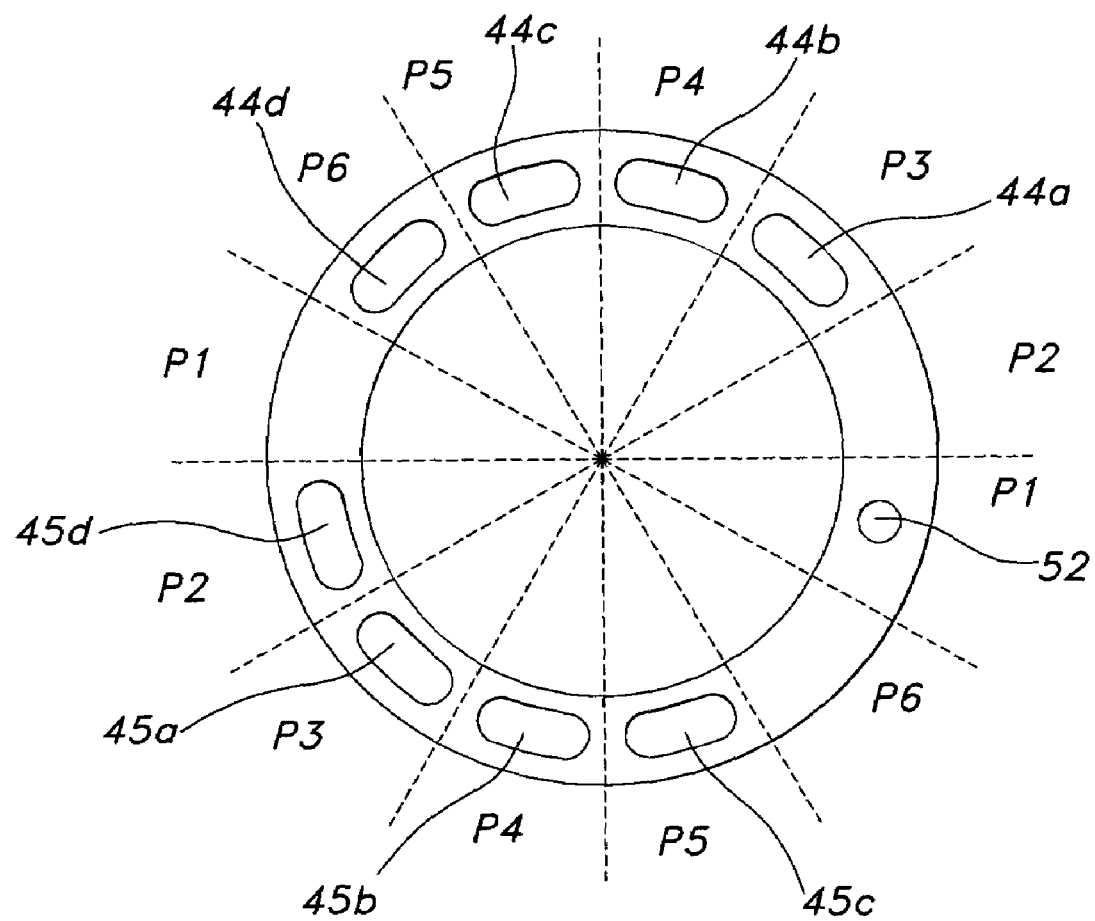
FIG. 4 is a diagrammatic illustration of an alternative embodiment of the FIG. 1 multilumen catheter so as to depict the passages therethrough.

Turning now to an alternative embodiment as shown in the cross-sectional view labeled FIG. 4, it may be seen that there are a total of six positions over each hemisphere of the tube 12. Each position is designated P1 though P6 respectively. Of course there may be more or less than six positions, the embodiment illustrated is simply meant to illustrate the concept in principle. Therefore, looking at each in turn it may be seen that the first position, or P1, contains the inflation lumen 52 and no corresponding ingression lumen or egression lumen 44 or 45 respectively. P2 contains egression lumen 45*d* but no corresponding ingression lumen. Positions P3, P4, and P5 contain each of a corresponding ingression lumen 44*a* and 45*a*, 44*b* and 45*b*, and 44*c* and 45*c* respectively. P6, similar to P1 contains an ingression lumen 44*d*, but no corresponding egression lumen.

Figure 5:
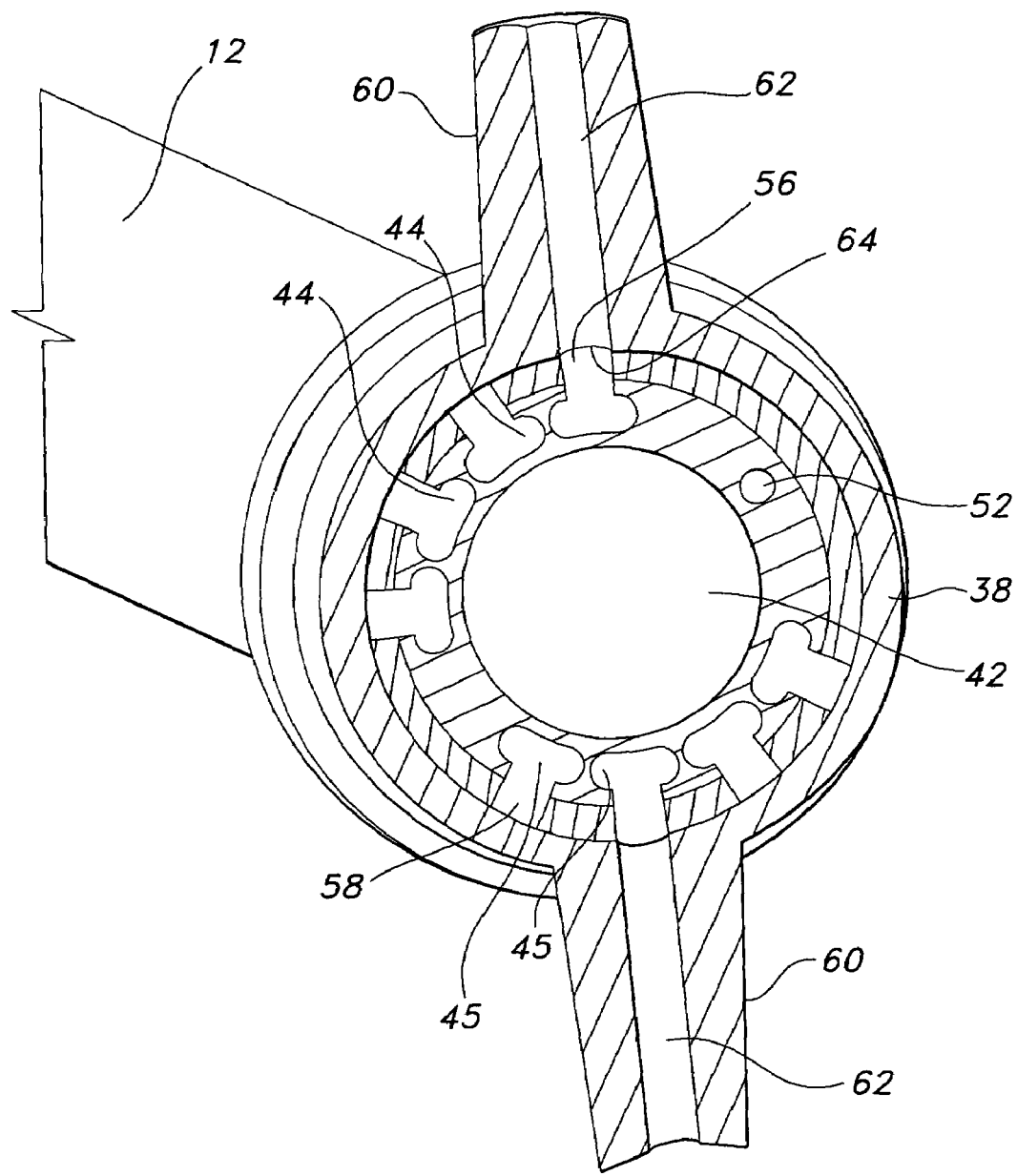
FIG. 5 is a cutaway of yet another alternative embodiment of the FIG. 1 multilumen catheter viewed through the axial centerline of the multilumen catheter so as to depict the passages therethrough.

FIG. 5 illustrates a partial cutaway view of the FIG. 4 embodiment. In this FIG., the collar 38 is also depicted, and together with the following description it should be evident to one skilled in the art as to the manner in which the device functions. As shown, the ingression and egression lumens 44 and 45 are radially disposed about the ventilation lumen 42. Each ingression lumen 44 contains an inlet 56, whereas each egression lumen 45 contains an outlet 58. The collar 38 has a dedicated conduit 60 for the ingression lumens 44 as well as a second dedicated conduit 60 for the egression lumens 45. Each conduit 60 is used to pass fluids into the patient 10 via ingression lumens 44, or to extract fluids from the patient 10 via egression lumens 45. Each conduit has a passage 62 leading from a point adjacent the second wall 48 to a point distal from the second wall. Rotating the collar 38 about the tube 12 selectively aligns the passage 62 within each conduit 60 with a specific ingression lumen 44 and its corresponding egression lumen 45 thus enabling flow into or out of the specific lumen as appropriate so that it may accomplish its intended function.

Looking at each position, P1 through P6, provides one with a better understanding of this particular embodiment of the invention. It may be seen that rotating the collar 38 so that the passages 62 in the conduits 60 are positioned at P1 effectively occludes both passages 62, and as such, no flow into or out of the cannula would take place. Rotating the collar 38 so that the passages 62 in the conduits 60 are positioned at P2 aligns one of the passages 62 with an egression lumen 45, in this case egression lumen 45*d*. The second passage 62 is occluded however and not aligned with an ingression lumen. This position enables the operator or medical personnel to suction fluids from the patient 10 without losing suction by having an open pathway through an ingression lumen 44. Rotating the collar 38 to any of positions P3, P4, or P5 aligns the passages 62 in the conduits 60 with; ingression lumen 44*a* and egression lumen 45*a*, ingression lumen 44*b* and egression lumen 45*b*, and ingression lumen 44*c* and egression lumen 45*c* respectively. Any of these orientations enable the operator to introduce fluids into the patient's respiratory system and to suction them out during the same operation. For example, the operator may wish to introduce an antimicrobial solution to reduce the potential for infection. In such instances it may be desirable to introduce the fluid and to suction it out in a relatively short period of time. P6 aligns one of the passages 62 with an ingression lumen 44, in this case egression lumen 44d. The second passage 62 is occluded however and not aligned with an egression lumen. This position enables the operator or medical personnel to introduce fluids, such as medication, into the patient 10 without immediately suctioning the medicine out of the patient 10. It can be seen on the FIG. 4 illustration that movement of the collar 38 over positions P1 through P6 accomplishes a partial revolution about the tube 12 of approximately 180 degrees.

The above description provides for a completely occluded position, P1, a suction only position, P2, and an introduction only position, P6, respectively. It should, however, be understood that the devices themselves that perform the suctioning and/or introduction of fluids do not form part of the invention and are thus not depicted. Nevertheless, each of these devices would likely be provided with means to enable or disable them. Additionally, it is not necessary that such devices be connected to either or both of the conduits 60. As such, fluid flow through any of the lumens may be controlled independently by the devices that are connected to either of the two conduits, irrespective of the intended function of the specific lumen. Through this, the embodiment depicted in FIG. 3 is capable of a no-flow position, a suction only position, and/or a discharge only position.

Figure 6:
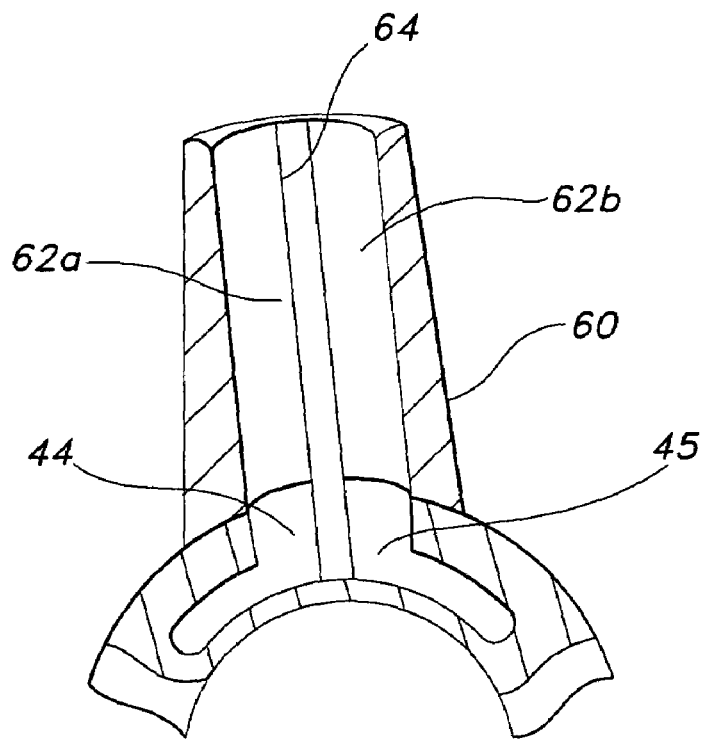
FIG. 6 is partial cutaway of yet another embodiment of the FIG. 1 multilumen catheter depicting one possible port configuration.

Yet another alternative embodiment as shown in FIG. 6 would enable 360 degree rotation of the collar 38 about the tube 12. In this embodiment, the collar 38 contains a single conduit 60 having separate passages 62a and 62b therethrough. These passages 62a and 62b are illustrated as being side-by-side and adjacent to one another, separated by a divider 64. However other arrangements such as coaxial are contemplated as well. In any event, the passages 62a and 62b align with lumens 44 and 45 respectively. Unlike in the FIGS. 3 and 4 embodiments which diametrically oppose the ingression lumens 44 with the egression lumens 45, this embodiment places them into paired arrangements which repeat about the circumference of the tube 12. An advantage of this embodiment is that irrigation or introduction of fluids may be made in very close proximity to suctioning should this be desirable or necessary and should the ports 40 and 41 be proximate to one another.

Figure 7:
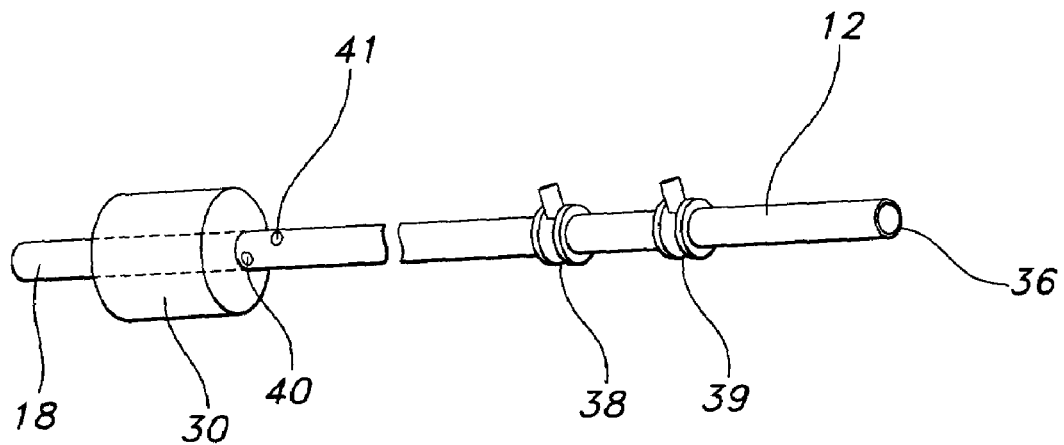
FIG. 7 is an isometric view of an alternative embodiment of the FIG. 1 multilumen catheter in a straightened configuration.

FIG. 7 depicts still another embodiment. In this embodiment, the ingression lumens 44 and the egression lumens 45 may be arranged in any suitable configuration, including those shown in FIGS. 3, 4, and 6. In this embodiment, however, a second collar 39 is provided. One collar, for example, collar 38 is adapted to align only with the inlets 56 of ingression lumens 44 whereas collar 39 is adapted to align only with the outlets 58 of ingression lumens 45. Otherwise, the collars 38 and 39 as well as the lumens 44 and 45 operate in the exact same manner as those described above.

It should be seen in any of the embodiments described above, that by rotating the collar 38 and/or 39 into a desired position, the user or medical personnel is provided with a selectable means with which to add or suction fluids from the patient 10. In some embodiments, the passage or passages 62 within the collar 38 may be configured to access more than one lumen 44 or 45 simultaneously.

Figure 8:
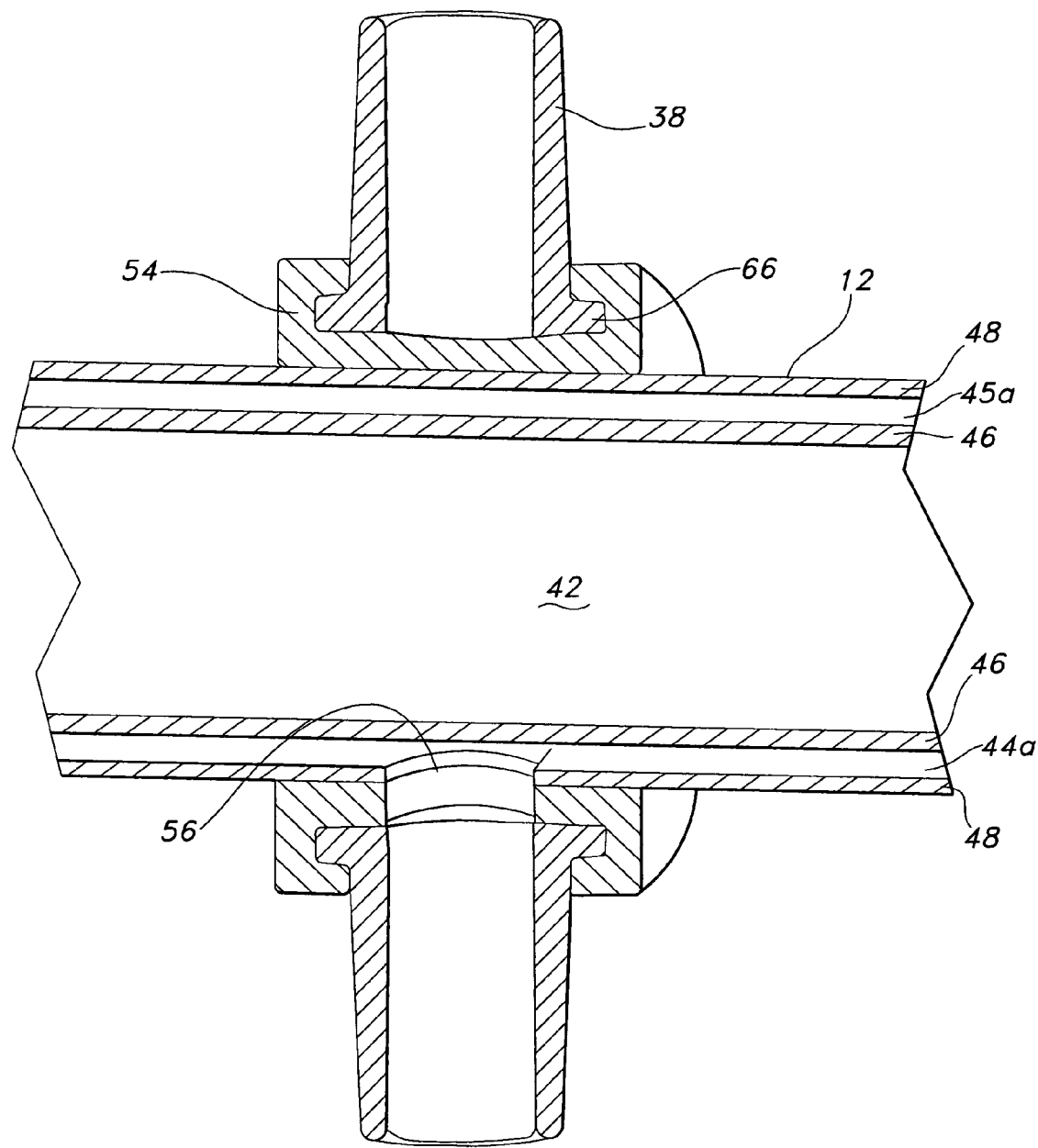
FIG. 8 is a side cutaway of the FIG. 1 multilumen catheter viewed through the radial centerline of the multilumen catheter, perpendicular to the FIG. 3 depiction, so as to depict the guide and collar.

Looking finally to FIG. 8, a partial cutaway view normal to the FIG. 3 view depicts the internal configuration of one embodiment of the collar 38 for additional clarity. This view depicts the tube 12, the ventilation lumen 42, one ingression lumen 44a separated from the ventilation lumen by the first wall 46 and bounded on the opposite side by the second wall 48. Likewise the corresponding egression lumen 45a is depicted as well. It too is separated from the ventilation lumen by the first wall 46 and bounded on the opposite side by the second wall 48. As is evident, the inlet 56 may be clearly seen as forming a passage through the second wall 48 into the ingression lumen 44a whereas the outlet 58 may be clearly seen as forming a passage through the second wall 48 into the egression lumen 45a. Details with respect to the guide 54 as well as the collar 38 may be seen. As can be seen, in some embodiments, the guide 54 is secured to the tube 12 such that rotational movement of the guide with respect to the tube is prevented. Appropriate measures should be taken to ensure that the collar 38 is capable of rotation with respect to the guide 54. For example, a flanged interface 66 between the two components may be used. Such an interface should be fluid tight so as not to enable air leakage into the system when suctioning or to have fluid leakage from the system to the environment. As such, those skilled in the art would understand and be capable of providing an appropriate fluid tight seal to these areas.

During use, the collar 38, and 39 if provided, would be rotated to the desired position. An indicator 68, for example, such as the one depicted in FIG. 3 may be provided. An indicator would enable a user to appropriately align the passage 62 within the conduit 60 with the desired lumen. As such, an indicator may be provided which corresponds to each lumen. In lieu or in addition, the collar 38 may be made to incrementally click, lock, or snap into each position. This may be accomplished by any number of means known to those with skill in the art. As can be seen from the FIGs. and from the detailed description each lumen is designed to operate in only one direction. This is to prevent cross contamination of the ingression lumens with the egression lumens as well as to minimize the need to backflush any one lumen thus preventing reintroduction of contaminants that coat any particular egression lumen 45. Additionally, in some embodiments, a one way valve (not shown) may be included, in the ingression path, the egression path, or both so as to prevent such cross contamination.

As used herein and in the claims, the term "comprising" is inclusive or open-ended and does not exclude additional unrecited elements, compositional components, or method steps.

While various patents have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

We claim:

1. A tracheal tube comprising:
 a cannula having a distal end and a proximal end; an inflatable cuff;
 at least one ingression lumen within the cannula having a suction port, the suction port located above the inflatable cuff;
 at least one egression lumen within the cannula in non-communication with the at least one ingression lumen, the at least one egression lumen having a discharge port, the discharge port located above the inflatable cuff on an outside surface of the cannula;

an inlet for introducing an externally applied therapeutic agent into the at least one ingression lumen; and an outlet for egress of fluids on the outside surface of the cannula from the at least one egression lumen.

2. The tracheal tube of claim 1 wherein the cannula comprises a first wall and a second wall concentric to the first wall, the first wall surrounding and defining a ventilation lumen adjacent a first surface, the first wall being attached at a second surface to a first surface of the second wall by at least two partitions, the at least one ingression lumen being defined by the second surface of the first wall, the first surface of the second wall, and first surfaces of the at least two partitions, and the at least one egression lumen being defined by the second surface of the first wall, the first surface of the second wall, and second surfaces of the at least two partitions.

3. The tracheal tube of claim 1 comprising any of a plurality of egression lumens, ingression lumens, or both.

4. The tracheal tube of claim 1 comprising a collar surrounding the cannula and overlapping each inlet and outlet, the collar being positionable so as to selectively enable and disable fluid communication through each lumen between its port and its inlet or outlet.

5. The tracheal tube of claim 1 comprising a first collar surrounding the cannula and overlapping the inlet, and a second collar surrounding the cannula and overlapping the outlet, each collar being positionable so as to selectively enable and disable fluid communication through each lumen between its port and its inlet or outlet.

6. The tracheal tube of claim 1, wherein the inflatable cuff surrounds the cannula at the distal end, the inflatable cuff adapted to seal the trachea of a patient, the inlet and outlet being proximal to the inflatable cuff.

7. A tracheal tube comprising:
a cannula having a distal end and a proximal end; an inflatable cuff;
a plurality of ingression lumens within the cannula, each having a suction port located above the inflatable cuff and an inlet located below the inflatable cuff;
a plurality of egression lumens within the cannula, each having a discharge port located above the inflatable cuff and an outlet located below the inflatable cuff, each ingression lumen is maintained in fluid non-communication with each egression lumen so as to minimize cross-contamination of any ingression lumen with any egression lumen;
a user manipulable selector for selectively enabling and disabling fluid flow through at least one of an ingression lumen, at least one of an egression lumen, or both.

8. The tracheal tube of claim 7 wherein the user manipulable selector comprises a rotatable collar rotatably affixed to the cannula and overlapping all of the inlets and outlets, the collar comprising a first and a second port therethrough, wherein rotation of the collar aligns the first port with the inlet of a user selected ingression lumen while automatically aligning the second port with the outlet of a corresponding egression lumen.

9. The tracheal tube of claim 8 comprising a guide coupled to the cannula overlapping all of the inlets and outlets, the guide having openings aligned with each inlet and outlet, the collar rotationally all ached to the guide.

10. The tracheal tube of claim 9 comprising a fluid tight seal between the collar and the guide.

11. The tracheal tube of claim 7 wherein the user manipulable selector comprises a first and a second rotatable collar each rotatably affixed to the cannula, the first collar overlapping all of the inlets, and the second collar overlapping all of the outlets, each collar having at least one port therethrough, wherein rotation of the first collar aligns the at least one port with the inlet of a user selected ingression lumen and rotation of the second collar aligns the at least one port with the outlet of a user selected egression lumen.

12. The tracheal tube of claim 11 comprising a guide coupled to the cannula overlapping all of the inlets and outlets, the guide having openings aligned with each inlet and outlet, the first and second collar rotationally attached to the guide and comprising a fluid tight seal between each collar and the guide.

13. The tracheal tube of claim 11 comprising a first and a second guide coupled to the cannula, the first guide overlapping all of the inlets, and the second guide overlapping all of the outlets, each guide having openings aligned with each inlet and outlet respectively, the first collar rotationally attached to the first guide and comprising a fluid tight seal between the collar and the guide, and the second collar rotationally attached to the second guide and comprising a fluid tight seal between the collar and the guide.

14. The tracheal tube of claim 7 wherein the ingression lumen enables the introduction of an externally applied therapeutic agent to be introduced into a patient within which the tracheal tube is placed.

15. The tracheal tube of claim 7 wherein the egression lumen enables the suctioning of fluids from a patient within which the tracheal tube is placed.

16. The tracheal tube of claim 7 comprising a ventilation lumen, the ingression and egression lumens being radially disposed about an outer diameter of the ventilation lumen.

17. The tracheal tube of claim 7, wherein the inflatable cuff surrounds the cannula at the distal end, the inflatable cuff adapted to seal the trachea of a patient, the inlets and outlets being proximal to the inflatable cuff, and an inflation lumen for selectively inflating and deflating the inflatable cuff.

18. The tracheal tube of claim 17 wherein any of the inlet and the outlet may be selectively occluded alone or in combination.

* * * * *